United States Patent [19]
Fukazawa et al.

[11] Patent Number: 4,814,458
[45] Date of Patent: Mar. 21, 1989

[54] PROCESS FOR PREPARING 4-ACETYL ISOQUINOLINONE COMPOUNDS

[75] Inventors: Nobuyuki Fukazawa; Tatsuo Kaiho; Hiroyuki Yamashita, all of Kanagawa, Japan

[73] Assignee: Mitsui Toatsu Chemicals, Inc., Tokyo, Japan

[21] Appl. No.: 10,304

[22] Filed: Feb. 2, 1987

[30] Foreign Application Priority Data

Feb. 12, 1986 [JP] Japan .................................. 61-26970

[51] Int. Cl.$^4$ ............................................ C07D 401/04
[52] U.S. Cl. .................................... 546/141; 546/330; 546/340; 546/341; 546/346
[58] Field of Search .......................................... 546/141

[56] References Cited

U.S. PATENT DOCUMENTS 3,480,634 11/1969 Finkelstein .......................... 546/141
4,639,521 1/1987 Sannohe et al. .................... 546/141

FOREIGN PATENT DOCUMENTS 61-291570 12/1986 Japan .
62-10063 1/1987 Japan .
62-4265 1/1987 Japan .
62-4266 1/1987 Japan .
62-5963 1/1987 Japan .

Primary Examiner—Glennon H. Hollrah
Assistant Examiner—James H. Turnipseed
Attorney, Agent, or Firm—Browdy and Neimark

[57] ABSTRACT

This invention relates to a novel process for preparing 4-acetyl-1-methyl-7-pyridyl-5,6,7,8-tetrahydro-3(2H)-isoquinolinone characterized by condensing 2-acetyl-4-pyridyl cyclohexanone with acetoacetamide. This compound is useful as pharmaceuticals, particularly cardiotonics.

4 Claims, No Drawings

PROCESS FOR PREPARING 4-ACETYL ISOQUINOLINONE COMPOUNDS

FIELD OF THE INVENTION

This invention relates to a novel process for preparing 4-acetyl isoquinolinone compounds useful as pharmaceuticals, especially cardiotonics, in particular, very useful 4-acetyl-1-methyl-7-pyridyl-5,6,7,8-tetrahydro-3(2H)-isoquinolinone.

BACKGROUND OF THE INVENTION

Many cardiac treating agents have been known as useful in the treatment of cardiac insufficiency. In particular, as the 4-acetyl isoquinolinone compounds, 4-acetyl-1-methyl-7-pyridyl-5,6,7,8-tetrahydro-3(2H)-isoquinolinone and the like have a high activity, as shown in Japanese Patent Application No. 144008/1985, and are useful cardiotonics having a wide safety range.

Conventionally, these 4-acetyl isoquinolinone compounds have been prepared by condensing 2-acetyl-4-pyridyl cyclohexanone with cyanoacetamide to produce 4-cyano-1-methyl-7-pyridyl-5,6,7,8-tetrahydro-3(2H)-isoquinolinone and then reacting the obtained compound with a Grignard reagent such as methyl magnesium iodide and the like followed by decomposition by an acid.

However, this conventional process is uneconomical as it requires many steps, and thus an economical process having shorter steps has been desired.

OBJECT OF THE INVENTION

It is an object of this invention to provide an economical novel process for preparing 4-acetyl-1-methyl-7-pyridyl-5,6,7,8-tetrahydro-3(2H)-isoquinolinone which is a 4-aceyl isoquinolinone compound extremely useful as a cardiotonic.

DISCLOSURE OF THE INVENTION

The object of this invention is as described above, and it can be achieved by reacting 2-acetyl-4-pyridyl cyclohexanone with acetoacetamide using no solvent or a proper solvent, without catalyst or in the presence of a base, to prepare 4-acetyl-1-methyl-7-pyridyl-5,6,7,8-tetrahydro-3(2H)-isoquinolinone.

Illustrating this invention in more detail, as shown in the following reaction routes, 2-acetyl-4-pyridyl cyclohexanone (I) synthesized by the method described in Japanese Patent Application Nos. 131940/1985, 142573/1985, 142574/1985 and 149165/1985 is reacted with acetoacetamide (II) using a proper solvent, which is preferably dissolved in a small amount thereof, although no solvent may be used.

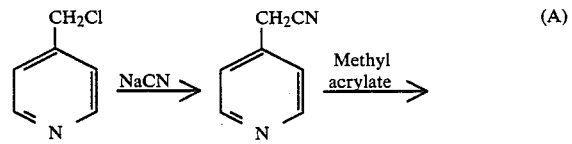

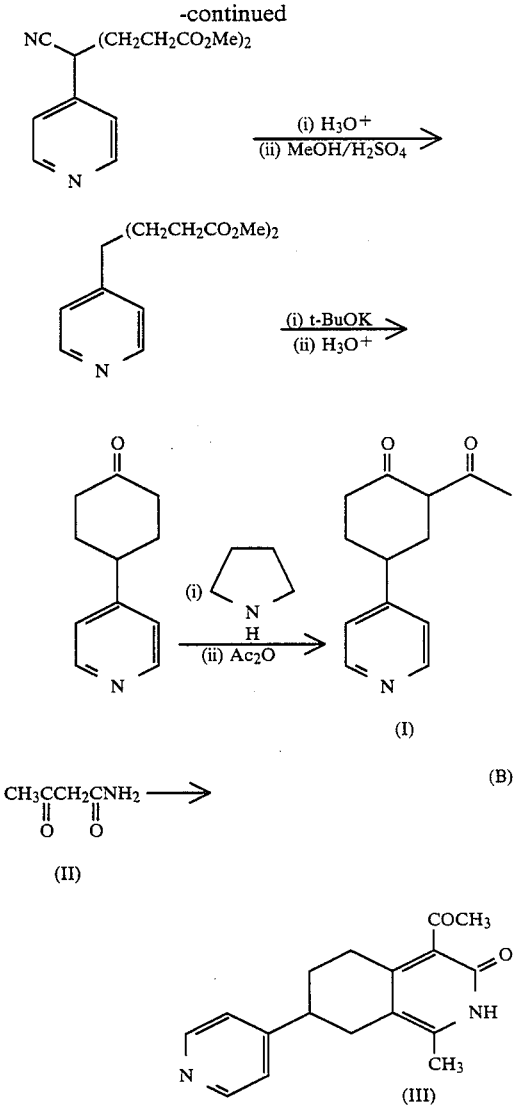

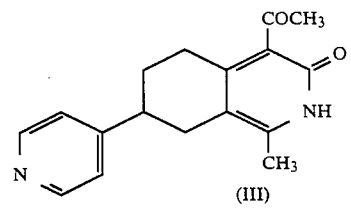

As the solvent, various solvents such as water, methanol, ethanol, propanol, tetrahydrofuran, chloroform, acetonitrile, pyridine, dimethylformamide and the like may be used alone or in the form of a mixture thereof.

The reaction proceeds without catalyst, but is preferably carried out in the presence of a base. Examples of the usable base include amine bases such as ammonia, methylamine, dimethylamine, diethylamine, triethylamine, pyrrolidine, piperidine, morpholine, 1,8-diazabicyclo[5,4,0]-7-undecene (hereinafter often referred to as D.B.U. for short), alkali metal bases such as sodium hydroxide, potassium hydroxide, potassium carbonate, sodium acetate and the like, and metal alcoholates such as sodium methoxide, sodium ethoxide, potassium butoxide and the like.

The reaction temperature can be selected between low temperatures and the boiling point of the used solvent, but the reaction is preferably carried out at a low temperature, if possible, as the quinoline compound (IV) represented by the following structural formula which is a by-product is produced in larger quantities as the temperature increases.

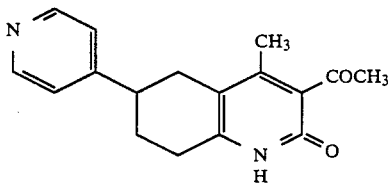

(IV)

However, when a secondary amine is used as the solvent, the by-product is less formed, compared with the cases when other solvents are used, even at a high temperature.

Also, the quinoline compound (IV) of the above by-product can be easily removed by recrystallization using a solvent such as methanol, ethanol, chloroform and the like.

The thus prepared 4-acetyl isoquinolinone compound has a strong cardiotonic effect. Particularly, 4-acetyl-1-methyl-7-(4-pyridyl)-5,6,7,8-tetrahydro-3(2H)-isoquinolinone (III) has an excellently strong cardiotonic effect and little side effects, and thus is useful as a remedy for cardiotonic insufficiency.

EXAMPLES

This invention is further concretely illustrated by Working Examples.

WORKING EXAMPLE 1

(a) Dimethyl 4-(4-pyridyl)-pimelate

In 400 ml of toluene was suspended 85 g of 4-(chloromethyl)pyridine hydrochloride (commercial product, the 1st grade), and the reaction mixture was neutralized by adding an aqueous solution of sodium hydroxide under ice cooling. After sufficient stirring, the resulting solution was separated, and 40 g of sodium cyanide and 200 ml of dimethyl sulfoxide (DMSO) were added to the toluene solution.

After stirring at 40° C. for 3 hours, 5 ml of 1,8-diazabicyclo[5,4,0]-7-undecene (D.B.U.) was added, and further 129 g of methyl acrylate was added dropwise thereto.

After completion of the addition, the resulting mixture was stirred at 40° C. for 1 hour and cooled with ice, and then 260 ml of water and 590 ml of toluene were added thereto. The mixture was stirred sufficiently and separated.

The toluene solution was taken out, and 700 ml of 10N hydrochloric acid was added thereto. After stirring, the solution was separated, and the separated hydrochloric acid solution was heated with stirring under reflux for 15 hours. The reaction mixture was concentrated under reduced pressure to remove water. To the residue were added 270 ml of methanol and 600 ml of toluene, and the mixture was stirred to remove the solvent. To the residue were added 650 ml of methanol and 13 g of conc. sulfuric acid, and the mixture was heated with stirring under reflux for 2 hours. After removal of the solvent, 500 ml of toluene was added to the residue, and further an aqueous solution of sodium hydroxide was added thereto to make the solution weakly alkaline. After stirring, the solution was extracted, and the toluene solution was dried with anhydrous Glauber's salt and filtered to remove the toluene under reduced pressure. As the residue, 90 g of dimethyl 4-(4-pyridyl)-pimelate was obtained.

The product obtained by purification through a silica gel column had the following physical property values.
IR $\nu_{cm^{-1}}^{max}$(film) 2950, 1740, 1600, 1435, 1250, 1200, 1170
NMR δ ppm (CCl$_4$) 1.7–2.2 (8H), 2.55 (1H), 3.58 (6H), 7.4 (2H), 8.6 (2H)

(b) 2-Acetyl-4-(4-pyridyl)-cyclohexanone

To a mixture of 800 ml of toluene and 70 g of potassium t-butoxide was added dropwise 90 g of dimethyl 4-(4-pyridyl)-pimelate obtained by the method (a) described above. After stirring at 40° C. for 2 hours, the reaction mixture was extracted by adding 650 ml of 6N hydrochloric acid.

The hydrochloric acid solution was heated with stirring under reflux for 2 hours, neutralized with an aqueous solution of sodium hydroxide and extracted using 800 ml of chloroform. The chloroform was removed under reduced pressure to afford 51 g of 4-(4-pyridyl)-cyclohexanone. The product purified through a silica gel column had the following physical property values.
IR $\nu_{cm^{-1}}^{max}$(film) 3010, 2920, 2860, 1700, 1600, 1400
NMR δ ppm (CDCl$_3$) 1.7–2.6 (m, 8H), 2.8–3.2 (m, 2H), 7.15 (m, 2H), 8.51 (m, 2H)

Then, 51 g of the thus obtained 4-(4-pyridyl)-cyclohexanone was dissolved in 350 ml of toluene, and 55 g of pyrrolidine was mixed therewith. The reaction mixture was heated with stirring to 80°–85° C. for 1 hour. After toluene-water azeotropic dehydration, toluene was removed. To the residue were added 390 ml of dioxane and 130 ml of acetic anhydride, and the mixture was heated with stirring at 40° C. for 10 hours. After addition of 240 ml of water, the mixture was heated at 100° C. for 1 hour and cooled, after which pH of the reaction mixture was adjusted to about 13 with an aqueous solution of sodium hydroxide. To the resulting solution was added 400 ml of chloroform, and the solution was separated after stirring.

To the aqueous layer was added 350 g of ammonium chloride, and the solution was extracted twice by adding 500 ml of chloroform. The chloroform solution was dried with anhydrous Glauber's salt and filtered, and the chloroform was removed under reduced pressure to afford 37 g of 2-acetyl-4-(4-pyridyl)-cyclohexanone. The product purified through a silica gel column had the following physical property values.
NMR δ ppm (CDCl$_3$) 1.7–2.2 (m, 3H), 2.16 (s, 3H), 2.3–2.6 (m, 3H), 2.6–2.9 (m, 1H), 7.10 (m, 2H), 8.55 (m, 2H), 15.7 (s, 1H)

(c) 4-Acetyl-1-methyl-7-(4-pyridyl)-5,6,7,8-tetrahydro-3(2H)-isoquinolinone

In 40 ml of 50% aqueous solution of dimethylamine was dissolved 20 g of the 2-acetyl-4-(4-pyridyl)-cyclohexanone obtained by the above method (b) under ice cooling, and 30 g of acetoacetamide was added thereto. After stirring at room temperature for 2 days, the reaction mixture was neutralized with 6N hydrochloric acid under ice cooling. After allowed to stand for 1 hour under ice cooling, the resulting mixture was filtered to afford 12 g of crude crystals containing 3–4% of the above-said quinoline compound (IV) which was impurities. The crude crystals were recrystallized with 300 ml of methanol to afford 8 g of purified 4-acetyl-1-methyl-7-(4-pyridyl)-5,6,7,8-tetrahydro-3(2H)-isoquinolinone. The physical property values were as follows.

mp. 296°–301° C. (decomposed)

IR $\nu_{cm^{-1}}^{max}$ (KBr) 2860, 1706, 1680, 1636, 1601, 1178

NMR δ ppm (CDCl$_3$) 1.6–3.1 (m, 7H), 2.35 (s, 3H), 2.62 (s, 3H), 7.18–7.28 (m, 2H), 8.50–8.60 (m, 2H), 13.68 (br.s. 1H)

WORKING EXAMPLE 2

In 20 ml of methanol was dissolved 11 g of the 2-acetyl-4-(4-pyridyl)-cyclohexanone obtained by the method described in Working Example 1(b), and 15 g of acetoacetamide was added thereto. Five milliliters of 28% sodium methoxide-methanol solution was added, and the mixture was stirred at room temperature for 2 days. After removal of the solvent, the reaction mixture was neutralized with 1N aqueous hydrochloric acid and extracted twice by adding 200 ml of chloroform.

The extracted solutions were combined and dried with anhydrous Glauber's salt, and then the chloroform was removed to afford 6.5 g of crude crystals.

The crude crystals were recrystallized with 200 ml of methanol to afford 4.5 g of 4-acetyl-1-methyl-7-(4-pyridyl)-5,6,7,8-tetrahydro-3(2H)-isoquinolinone. The physical property values of this product also sufficiently accorded with those described in (c) of Working Example 1.

WORKING EXAMPLE 3

In a mixed solvent of 10 ml of water and 10 ml of methanol was dissolved 10.9 g of the 2-acetyl-4-(4-pyridyl)-cyclohexanone obtained in Working Example 1(b), and 15 g of acetoacetamide and further 6.9 g of potassium carbonate were added thereto.

After the reaction mixture was stirred at room temperature for 2 days, the solvent was removed and the resulting solution was neutralized with 1N hydrochloric acid. The crystallized crystals were filtered to afford 6.5 g of crude crystals. The crude crystals were recrystallized with 200 ml of methanol to afford 3.9 g of 4-acetyl-1-methyl-7-(4-pyridyl)-5,6,7,8-tetrahydro-3(2H)-isoquinolinone.

The physical property values of this product also sufficiently accorded with those described in Working Example 1.

WORKING EXAMPLE 4

In 20 ml of chloroform was dissolved 10.9 g of the 2-acetyl-4-(4-pyridyl)-cyclohexanone obtained by the method of Working Example 1(b), and 15 g of acetoacetamide and further 2 ml of D.B.U. were added thereto.

After the reaction mixture was stirred at room temperature for 2 days, 200 ml of chloroform was added thereto. The mixture was washed with water and the chloroform solution was dried with anhydrous Glauber's salt. The chloroform was removed to afford 7.1 g of crude crystals. The crude crystals were recrystallized with 200 ml of methanol to afford 4.3 g of purified 4-acetyl-1-methyl-7-(4-pyridyl)-5,6,7,8-tetrahydro-3(2H)-isoquinolinone. The physical property values of this product also sufficiently accorded with those described in Working Example 1.

WORKING EXAMPLE 5

In 40 ml of diethylamine was dissolved 20 g of the 2-acetyl-4-(4-pyridyl)-cyclohexanone obtained by the method of Working Example 1(b), and the mixture was stirred at room temperature for 30 minutes.

Thirty grams of acetoacetamide was added thereto, and the reaction mixture was stirred at room temperature for 12 hours and further heated with stirring at 45° C. for 18 hours.

After removal of diethylamine, 300 ml of water was added to the residue and the solution was neutralized with 6N hydrochloric acid. The crystallized crystals were filtered to afford 12.8 g of the crude crystals. The crude crystals were recrystallized with 300 ml of methanol to afford 9.3 g of purified 4-acetyl-1-methyl-7-(4-pyridyl)-5,6,7,8-tetrahydro-3(2H)-isoquinolinone. The physical property values of this product also sufficiently accorded with those described in Working Example 1.

WORKING EXAMPLES 6–10

Using one kind of toluene, pyridine, acetonitrile, tetrahydrofuran, and ethanol as the solvent, 10.9 g of the 2-acetyl-4-(4-pyridyl)-cyclohexanone obtained by the method of Working Example 1(b) was dissolved in 20 ml thereof, respectively, and 20 g of any one base selected among D.B.U., sodium methoxide, diethylamine, potassium carbonate, and sodium hydrogencarbonate was added thereto. Then, 15 g of acetoacetamide was added to the reaction mixture, and the mixture was stirred at room temperature for 2 days.

After removal of the solvent, 100 ml of water was added and the resulting solution was neutralized with 1N hydrochloric acid. The crystallized crystals were filtered to afford 6.4 g of crude crystals. The crude crystals were recrystallized with 200 ml of methanol to afford about 4 g of purified 4-acetyl-1-methyl-7-(4-pyridyl)-5,6,7,8-tetrahydro-3(2H)-isoquinolinone in every case. The physical properties values of each obtained product also sufficiently accorded with those described in Working Example 1.

What is claimed is:

1. A one-step process for preparing 4-acetyl-1-methyl-7-pyridyl-5,6,7,8-tetrahydro-3(2H)-isoquinolinone, which comprises condensing 2-acetyl-4-pyridyl cyclohexanone with acetoacetamide.

2. A process according to claim 1 carried out in the presence of a base.

3. A process according to claim 1 carried out in the presence of a secondary amine as a solvent.

4. A process according to claim 1 wherein said condensing is carried out at a temperature no greater than about room temperature.

* * * * *